United States Patent

Levander

Patent Number: 5,728,075
Date of Patent: Mar. 17, 1998

[54] INJECTION DEVICES

[75] Inventor: Gustav Levander, Bromma, Sweden

[73] Assignee: Pharmacia & Upjohn Aktiebolag, Stockholm, Sweden

[21] Appl. No.: 464,875

[22] PCT Filed: Oct. 10, 1994

[86] PCT No.: PCT/SE94/00950

§ 371 Date: Aug. 14, 1995

§ 102(e) Date: Aug. 14, 1995

[87] PCT Pub. No.: WO95/11711

PCT Pub. Date: May 4, 1995

[30] Foreign Application Priority Data

Oct. 29, 1993 [SE] Sweden ............................ 9303568

[51] Int. Cl.⁶ .................................................. A61M 5/50
[52] U.S. Cl. ................................. 604/211; 604/224
[58] Field of Search ............................ 604/211, 187, 604/224, 228, 82, 89, 90, 91, 218, 232, 241, 207, 208, 210

[56] References Cited

U.S. PATENT DOCUMENTS

| | | | |
|---|---|---|---|
| 562,425 | 6/1896 | Scheever | 604/232 X |
| 2,130,305 | 9/1938 | Lewis | 604/232 X |
| 2,283,915 | 5/1942 | Cole | 604/211 |
| 2,736,315 | 2/1956 | Feeney | 604/211 |
| 4,189,065 | 2/1980 | Herold | 222/46 |
| 4,710,179 | 12/1987 | Haber et al. | 604/211 |
| 4,810,249 | 3/1989 | Haber et al. | 604/210 |
| 5,080,649 | 1/1992 | Vetter | 604/91 |
| 5,344,409 | 9/1994 | Ennis, III et al. | 604/210 |
| 5,380,295 | 1/1995 | Vacca | 604/187 |
| 5,468,232 | 11/1995 | Naganuma | 604/200 |

FOREIGN PATENT DOCUMENTS

| | | |
|---|---|---|
| 0 265 876 A2 | 4/1988 | European Pat. Off. . |
| 0 440 846 A1 | 2/1990 | European Pat. Off. . |

*Primary Examiner*—Michael Powell Buiz
*Assistant Examiner*—A. T. Nguyen
*Attorney, Agent, or Firm*—Pollock, Vande Sande & Priddy

[57] ABSTRACT

A piston rod device for use in an injection device for an injection cartridge is provided with a single or multiple thread (3) along a predetermined portion of its length, after which the thread (3) changes into a longitudinal groove (5) for each thread, such that a turning movement of the piston rod will turn into an axial movement after the predetermined length. The thread (3) is shaped as one or more helicoidal grooves in the surface of the piston rod (1), the grooves (3) turning into longitudinal grooves (5) after the predetermined length. A nut element (6) cooperates with the thread (3), and its device for cooperating consists of at least one radial inwardly directed projection (10) for each thread, the projection (10) or projections guiding the piston rod (1) by the groove or grooves forming the thread (3).

6 Claims, 3 Drawing Sheets

INJECTION DEVICES

DESCRIPTION

1. Technical Field

The present invention refers to improvements in injection devices for adminstering a liquid preparation by injection. More particularly, the invention refers to improvements in injection devices for injection cartridges, and especially then in injection devices for multi-chamber injection cartridges. Still more particularly, the invention refers to a novel device in a piston rod for use in an injection device employing an injection cartridge.

2. Background Art

Injection devices using injection cartridges have been known for a long time and have been appreciated for their ease of handling and their lessened risk of contamination of the preparation to be injected. An injection cartridge is essentially shaped as a cylinder which is filled with the liquid injectable preparation. The front end of the cylinder is sealed by a closure which may be pierced by an outlet conduit, such as an injection needle, when the preparation is to be injected. The rear end of the cartridge is sealed by a piston which may be urged forward by means of a piston rod acting thereon. This piston will then expel the preparation from the cartridge through the outlet conduit. The cartridge is usually arranged in a holder device which comprises the piston rod for acting on said piston. The holder device may also comprise a mechanism for setting and delivering one or more predetermined doses of the preparation to be injected.

A further development of the injection cartridges has been the so-called multi-chamber cartridges. Such cartridges are intended to be used for injectable preparations where the ready-to-use preparation is not stable for any extended time, and are divided into a front chamber and a rear chamber, which are separated by an intermediate movable wall. The front chamber usually contains a solid component of an injectable preparation, while the rear chamber contains a liquid component of said preparation. At a suitable position in the cartridge, a bypass connection is arranged in the interior wall of the cartridge, such that the liquid component may flow around and bypass the intermediate wall, to be mixed with the solid component.

When the mixing of the two components is to be carried out, pressure is applied to the piston by means of a piston rod, to urge it forward. The pressure is transmitted through the liquid in the rear chamber such that the intermediate movable wall is also urged forward. When the intermediate wall has been moved forward for a predetermined distance, it will be positioned at the bypass connection, making it possible for the liquid component to bypass the intermediate wall to flow into the front chamber. Further movement forward of the piston will cause the liquid component to flow over into the front chamber until all of the liquid has been transferred into the front chamber, and the front face of the piston rests against the rear face of the intermediate wall. The liquid component will now be mixed with the solid component to be dissolved or suspended in the liquid phase.

Further forward pressure on the piston will now move it together with the intermediate wall forward together to expel the mixed injectable preparation from the front chamber of the cartridge through the outlet conduit in the front closure of the cartridge.

The design and function of injection cartridges of the single-chamber and the multi-chamber type is well-known to those skilled in the art and does not have to be described here in greater detail.

When a dual-chamber injection cartridge is to be readied for injection, it is important that the piston is displaced smoothly without any uneven movements. Furthermore, it is important that the forward movement is stopped just at the exact position where the piston and the intermediate wall contact with each other and all the liquid has passed over into the front chamber. For this, the piston rod is often provided with a thread which cooperates with a corresponding internal thread in a nut element provided in a holder device for the cartridge. Thus, the piston rod is smoothly advanced forward by the screw movement, and the threaded portion of the piston rod can be terminated when the piston rod has reached its correct forward position for a completed mixing of the components. After this, the piston rod can be moved forward by a straight movement in the axial direction, when the mixed injectable preparation is to be expelled from the front chamber. Such an arrangement is known from EP-A1-0 328 699.

This known arrangement, however, has a number of shortcomings and room remains for certain improvements. Thus, in the known device, there is no definite stop for the turning movement of the piston rod when the piston has reached its correct position after the mixing, and the user gets no clear indication about this. The average user will therefore turn the piston rod around for a few extra turns to be sure that the injectable preparation has been reconstituted correctly. This is an inconvenience. Furthermore, when the threaded part of the piston rod has passed through the nut element in the holder device, there will be a considerable play between the unthreaded part of the piston rod and the nut element. This may cause a wobble of the piston rod when an injection is administered, which may be quite uncomfortable to the patient.

SUMMARY OF INVENTION

The shortcomings mentioned above are eliminated by the improvements according to the present invention. According to the invention, there is provided a device in a piston rod for use in an injection device for an injection cartridge, wherein a helicoidal movement after a predetermined length is changed into a linear movement in the longitudinal direction, and comprising a single or multiple thread along a predetermined length of the piston rod, and a nut element which cooperates with the thread. What characterizes the invention is that the thread or threads on the piston rod is shaped as one or more helicoidal grooves in the surface of the piston rod, each of said thread or threads after the predetermined length turning into a longitudinal groove in the surface for each thread, and that the device in the nut element for cooperating with the thread consists of at least one inwardly directed radial projection for each thread, the projection or projections guiding the piston rod by the groove or grooves forming the thread or threads.

In a preferred embodiment of the invention, the piston rod is provided with a double or triple thread, or in other words, has two or three helicoidal grooves in its core, such that a double or triple thread is formed. The nut element is then correspondingly provided with two or three inwardly directed radial projections, which are evenly distributed along the internal circumference of said nut element. It is clear that the piston rod may also be provided with more than three threads, such as four or five, although no important functional advantages will be gained by this. The dimensions of the device may also be a limiting factor.

In a further preferred embodiment, the external diameter of the piston rod is adapted to the internal diameter of the nut element such that the piston rod fits slidably in the nut element without any substantial radial play.

In a still further preferred embodiment, the injection cartridge is a multi-chamber injection cartridge.

BEST AND VARIOUS MODES FOR CARRYING OUT INVENTION

Figure 1:
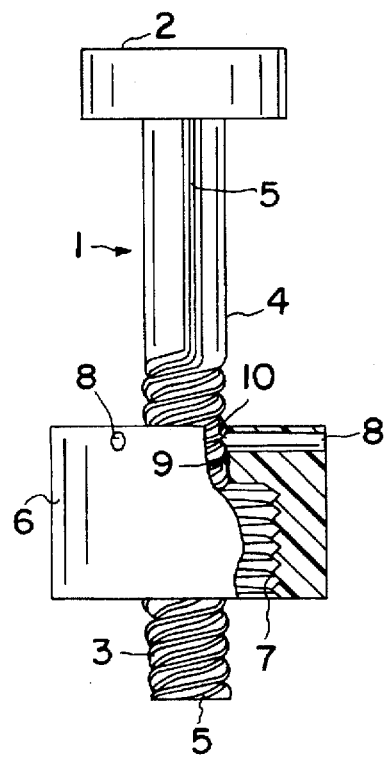
FIG. 1 shows a piston rod according to the invention with its threaded part in cooperation with a nut element.

In FIG. 1, the piston rod 1 has a head 2, the edge of which may be knurled for easier gripping. Other means for convenient gripping may also or alternatively be provided, such as a cross-bar. At the opposite part from the head 2, the piston rod 1 has a thread 3, which consists of one or more helicoidal grooves in the rod. This means that the top of the thread has the same diameter as the unthreaded portion 4 of the piston rod 1. After a predetermined distance from the threaded end 5 of the piston rod 1, each thread 3 turns into a groove 5 in the longitudinal direction of the piston rod 1. This longitudinal groove 5 has the same size as the groove or grooves which form the thread or threads 3, and runs for a predetermined distance or preferably all the way to the head 2.

The groove or grooves in the piston rod 1 cooperate with a nut element 6. This nut element may be shaped like a cap with its open end facing in the direction of the threaded end 5. The internal wall of the cap may be provided with a thread 7 for attaching to a corresponding thread at the rear end of an injection device. However, other conventional attachment devices are also possible.

According to the invention, the nut element 6 cooperates with the thread 3 and the groove 5 in the piston rod 1 by means of at least one radial projection or pin 8 arranged in said nut element 6. The pin 8 projects from the internal wall 9 of the nut element 6 and its projecting end 10 has such a shape that it matches the shape of the groove forming the thread 3 and the subsequent longitudinal groove 5. Thus the pin 8 serves as a guide for the thread 3 and the longitudinal groove 5 and consequently also for the movement of the piston rod 1. The projection 8 may be formed by a pin which goes through the wall of the nut element 6, as shown in the drawing, or it may be integral with the nut element 6 and project from its internal wall 9.

In a preferred embodiment, the thread 3 comprises two or three grooves, such that a double or triple thread is formed. In such a case, there is one pin 8 arranged in the nut element 6 for each groove. There may also be arranged two or more guiding pins 8 in each groove, to provide a more secure guidance of the piston rod 1.

The internal wall 9 of the nut element 6 has a diameter which is closely matched to the external diameter of the piston rod 1 such that a close sliding fit is obtained. Through the design of the thread 3 as one or more helicoidal grooves in the piston rod 1, this close fit is maintained both when its threaded part 3 is positioned in the nut element 6 and when the part having the longitudinal groove or grooves is positioned within said nut element 6, and there will be no loose fit or wobble between the piston rod and the nut element at any time. This is an important feature of the invention.

Figure 2:
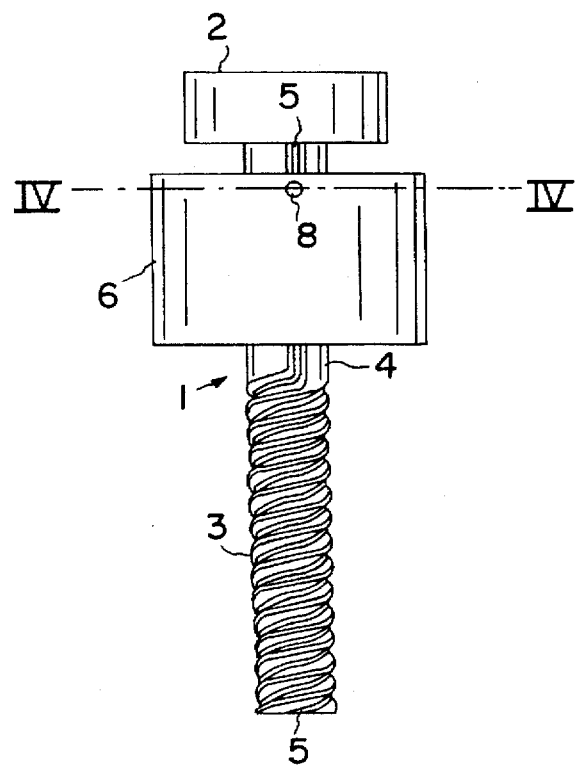
FIG. 2 shows the piston rod with the nut element cooperating for an axial movement.

FIG. 2 shows the same combination of piston rod 1 and nut element 6. Here the piston rod 1 has been advanced by the thread 3 through the nut element 6 so far that said nut element is positioned around the unthreaded portion 4 of said piston rod 1. The inwardly projecting part of the guide pin 8 is now positioned in the longitudinal groove 5 such that the piston rod 1 is now guided in a straight longitudinal movement. As the unthreaded portion 4 of the piston rod 1 has the same external diameter as the top of the thread 3, there is still a close sliding fit between the piston rod 1 and the internal wall of the nut element 6, and no wobble is possible. This is an important advantage of the invention.

Figure 3:
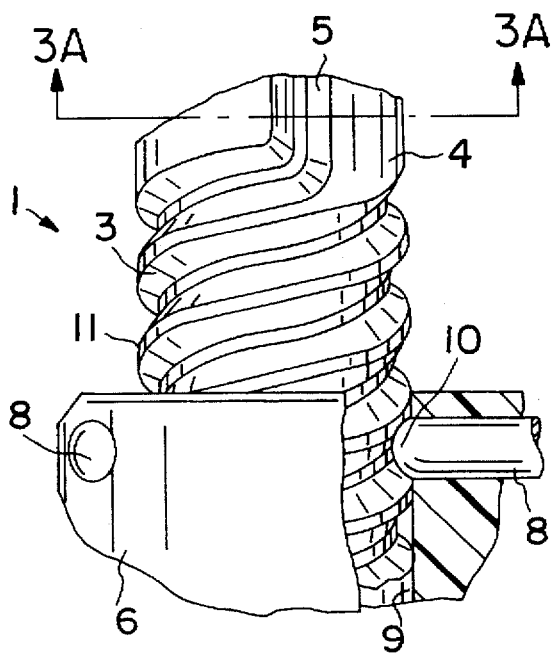
FIG. 3 shows a an enlarged partial view of the nut element cooperating with the threaded part of the piston rod.

FIG. 3 shows an enlarged portion, partly sectioned, of the arrangement shown in FIG. 1. The piston rod 1 is positioned with its thread 3 inside the nut element 6. The guide pin 8 has its inwardly projecting part 10 positioned in the groove which forms the thread 3 such that said projection 10 guides the thread 3 through the nut element 6. The groove 3 which forms the thread turns into a longitudinal groove 5 after a predetermined distance from the end of the piston rod 1. This longitudinal groove 5 has the same dimensions as the thread-forming groove 3, such that the projection 10 of the guide pin 8 fits there equally well.

The top of the thread 11 has the same diameter as the unthreaded part 4 of the piston rod 1 and fits snugly inside the nut element 6, such that a close sliding fit is obtained between the outside 4,11 of the piston rod 1 and the inside 9 of the nut element 6. This will give a secure guidance of the piston rod along its complete length.

Figure 4:
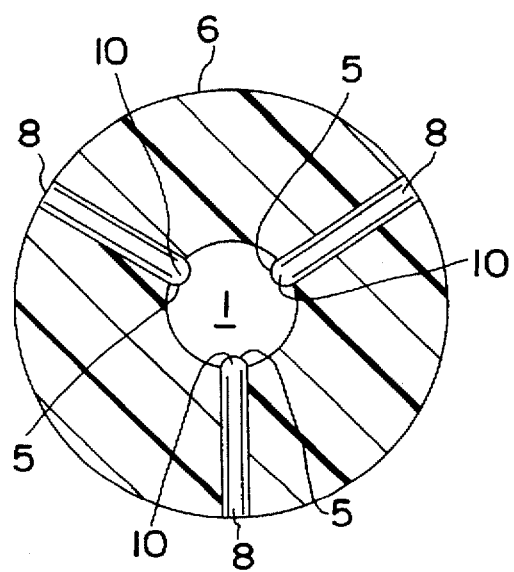
FIG. 4 is a sectional view along the line IV—IV in FIG. 1.
Figure 4A:
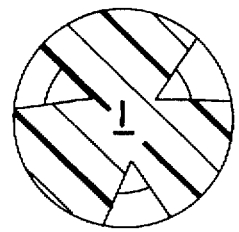
FIG. 4A shows a cross-sectional view of the piston rod where the grooves are shown as triangular.

FIG. 4 is a sectional view along IV—IV in FIG. 2. It is seen that three radial guide pins 8 are arranged with uniform peripheral spacing in the nut element 6. The inwardly projecting ends 10 of said pins 8 rest in the three longitudinal grooves 5. Preferably the longitudinal grooves 5 have a trapezoidal or triangular cross-section (e.g., FIG. 4A schematically shows the triangular cross section), while the projecting ends 10 of the pins 8 are rounded. This will give a point contact between said projecting ends 10 and the walls of the grooves 5, which will give a lower friction. It is also seen that the piston rod 1 fits snugly inside the nut element 6. This fit must be sufficiently loose to permit the piston rod 1 to slide and rotate easily inside the nut element 6, as guided by the pins 8, but the fit must be sufficiently close to prevent any wobble of the piston rod 1 inside the nut element 6.

Figure 5:
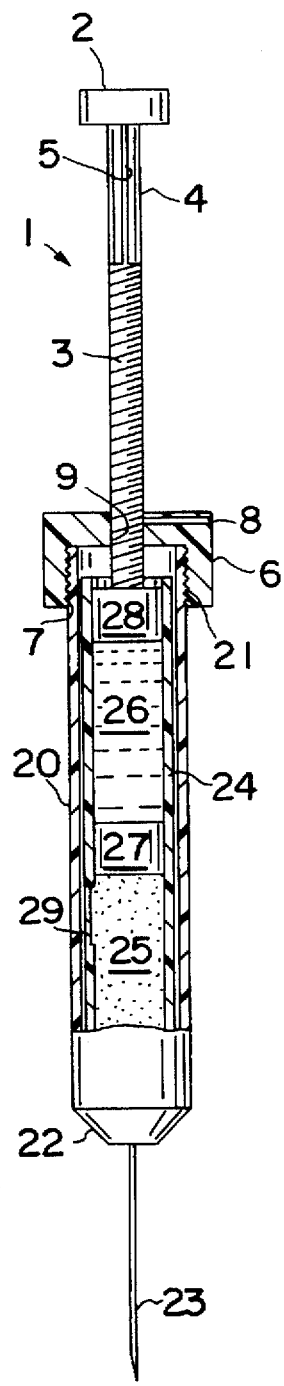
FIG. 5 shows the piston rod and the nut element of the invention, arranged in an injection device and before the cartridge is readied for an injection.

FIG. 5 shows the piston rod and nut element according to the invention arranged in an injection device before said device has been readied for injection. The injection device comprises a tubular sleeve 20 which is provided with an external thread 21 at its rear end. At its front end 22, the sleeve is adapted to receive an injection needle or cannula 23 in a conventional manner. Inside the tubular sleeve 20 is arranged an injection cartridge 24 of the dual-chamber type. The cartridge 24 is divided into a front chamber 25, which contains a solid component of an injectable preparation, and a rear chamber 26, which contains a liquid component of the same injectable preparation. The two chambers 25 and 26 are separated by a movable wall 27, which may be displaced and act as a piston. The rear chamber 26 is sealed at its rear end by a piston 28, which may be moved forward by means of a piston rod. At the front end of the front chamber 25, a connection of a conventional type is arranged with the injection needle 23 such that the injectable preparation may be expelled through said needle.

At a predetermined position in the interior wall of the cartridge 24 is arranged a bypass connection 29. When the movable wall 27 is positioned at this bypass connection 29, the liquid component can flow over into the front chamber 25, bypassing the movable wall 27.

The design and function of dual-chamber injection cartridges are conventional, and need not be described here in closer detail. It should be noted, however, that the cartridge may also comprise more than two chambers, for example three chambers, which may contain different components.

The external thread 21 at the rear end of the tubular sleeve 20 cooperates with the internal thread 7 of the nut element 6 such that this nut element with the piston rod 1 may be screwed onto the tubular sleeve. In the starting position, before the cartridge has been readied for the administration of an injection, the threaded portion 3 of the piston rod 1 is positioned within the nut element 6, and the front end 5 of the piston rod 1 is resting on the rear face of the piston 28.

Figure 6:
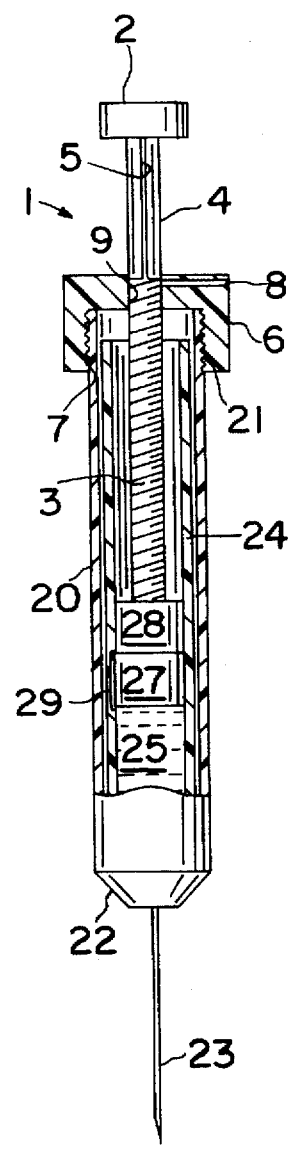
FIG. 6 shows the piston rod and the nut element of the invention, arranged in an injection cartridge which has been readied for injection. In all the figures, like parts have the same reference numbers.

FIG. 6 shows the piston rod and nut element of the invention arranged in an injection device where said injection device has been readied for an injection. The piston rod 1 has now been screwed forward by turning the head 2, and the thread 3 has been guided by the guide pins 8 in the nut element 6 such that the front end of the piston rod 1 has been advanced into the tubular sleeve 20 and the injection cartridge 24. The front end of the piston rod 1 has then acted on the piston 28 to urge it forward, and this forward movement has been transmitted through the liquid component in the rear chamber 26 such that the movable wall 27 has also been moved forward. When this movable wall 27 has reached the position of the bypass connection 29, further forward movement of the piston 28 has made the liquid component flow through said bypass connection to be mixed with the solid component in the forward chamber 25, to form the desired injectable preparation.

After all of the liquid component has been made to flow over into the front chamber 25, the front face of the piston 28 will rest against the rear face of the movable wall 27. At this position of the piston 28, the piston rod 1 has been advanced so far that the threaded portion 3 on it has ended and the thread or threads 3 have turned into one or more longitudinal grooves 5 in the unthreaded portion 4 of the piston rod. Thus no more rotational movement is possible, and this shows the user that the piston 28 has been advanced sufficiently far to effect a correct reconstitution of the injectable preparation. The length of the threaded portion 3 of the piston rod 1 is adapted to the dimensions of the injection cartridge such that this is achieved. The injection device is now ready for administration.

On further forward pressure on the piston 28, the piston 28 and the movable wall 27 will act as a single piston to expel the ready-mixed injectable preparation from the injection cartridge 24 through the injection needle or cannula 23. This forward pressure is effected by pushing the piston rod 1 forward by means of its head 2. The forward movement of the piston rod 1 will be guided by the guide pins 8 in the longitudinal grooves 5. As the threaded portion 3 and the unthreaded portion 4 of the piston rod 1 have the same diameter and fit snugly against the internal wall 9 of the nut element 6, there will always be a close sliding fit between the piston rod 1 and the nut element 6. The piston rod 1 will be securely guided, and no wobble will be possible during the administration of the injectable preparation. This is a clear advantage of the present invention against the prior art.

It is to be noted that the the injection device shown in cooperation with the piston rod and nut element device of the invention is only an example, and that many other embodiments are apparent to those skilled in the art. For example, the injection device may be provided with a dosing device for setting and metering out a number of doses of the injectable preparation. A number of such dosing devices are known from the prior art.

In one embodiment, the threaded portion of the piston rod may comprise a snap lock mechanism which cooperates with one or more of the inwardly directed projections of the nut element. Such mechanisms are known per se from the prior art, and are especially to be used in disposable injection devices, which are only to be used once and then be discarded. With such a snap lock mechanism, it will not be possible to unscrew the piston rod to insert a new injection cartridge. This is an important safety feature.

Figure 3A:
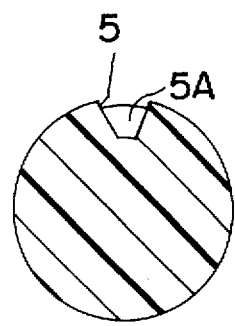
FIG. 3A is a schematic illustration of the snap lock mechanism.

FIG. 3A illustrates a snap lock mechanism. Here, the structure 5A is simply an inclined surface in the groove 5, which may easily be overridden by the pin 8 when the piston rod is moved in the direction of injection, but which stops an undesired movement rearward.

The dimensioning of the piston rod and nut element arrangement according to the invention should be adapted to the dimensions of the multi-chamber injection cartridge used. Such cartridges are usually provided in standard dimensions to fit standard injection devices. Thus the dimensioning of the piston rod, especially the length of its threaded portion, and the nut element can easily be determined by a person skilled in the art and having knowledge of the present invention and its application.

Also, the selection of suitable materials for the piston rod and nut element of the invention does not present any difficulties to a person skilled in the art. Generally, various plastic materials are used, such as polyolefins, for example polyethylene or polypropylene, or halogenated polyolefins, for example polyvinyl chloride or fluorinated polyolefins, or nylon, polyesters or polycarbonates. The guide pins can be made of stainless steel, if they are not integral with the nut element.

A further advantageous feature of the invention is that the device of the invention may be manufactured in a simple and inexpensive way from inexpensive materials. The manufacturing of the thread and the axial groove in the piston rod may be carried out with conventional apparatus. Furthermore, there is no need to make an internal thread in the nut element for guiding the piston rod. This makes the device well adapted to be used in disposable injection devices.

In the foregoing, the invention has been described with reference to examples shown in the drawing. It is to be noted that these examples only serve to illustrate the invention, and do not limit it in any way. Various modifications and variations of the invention are possible within the scope of the appended claims.

What is claimed is:

1. A device for use in an injection device for a dual-chamber or multi-chamber injection cartridge, wherein said device comprises a cartridge having a front chamber and a rear chamber separated by an intermediate movable wall, said front chamber being adapted for holding a solid component of an injection preparation and said rear chamber being adapted for holding a liquid component of said preparation; said cartridge further includes an interior wall and has arranged in said interior wall a bypass connection for permitting the liquid to flow around and bypass said intermediate movable wall for mixing with the solid component; and wherein said device further comprises a piston rod having a single or multiple thread along a predetermined length thereof, and a nut element which cooperates with said thread and being adapted for applying pressure through the liquid in said rear chamber for also urging said intermediate movable wall forward to position it at said bypass connection thereby making it possible for the liquid component to bypass said intermediate movable wall and flow in said front chamber to be mixed with the solid component; and wherein further forward pressure on said piston rod moves it together with said intermediate movable wall for expelling the injectable preparation from said front chamber through an outlet conduit in the front chamber; wherein said thread on the piston rod is shaped as at least one helicoidal groove in the surface of said piston rod, each groove after the predetermined length turning into a longitudinal groove in said surface, such that a helicoidal movement of said piston rod for said predetermined length is changed into a linear movement in the longitudinal direction, and that the device in the nut element for cooperating with said thread consists of at least one inwardly directed radial projection for each thread, said projection or projections guiding said piston rod by the groove or grooves forming said thread.

2. A device according to claim 1 characterized in that the external diameter of the piston rod is adapted to the internal diameter of the nut element such that the piston rod fits slidably in the nut element without any substantial radial play.

3. A device according to claim 1 characterized in that the piston rod is provided with a double thread and that the nut element is provided with two corresponding, inwardly directed radial projections, which are evenly spaced along the internal circumference of said nut element.

4. A device according to claim 1 characterized in that the piston rod is provided with a triple thread and that the nut element is provided with three corresponding, inwardly directed radial projections, which are evenly spaced along the internal circumference of said nut element.

5. A device according to claim 1 characterized in that the groove or grooves in the piston rod have a trapezoidal or triangular cross-section.

6. A device according to claim 1, wherein the threads of the piston rod are arranged as a snap lock mechanism, which cooperates with the projection or projections in the nut element.

* * * * *